United States Patent [19]

Goertz et al.

[11] Patent Number: 4,801,460

[45] Date of Patent: Jan. 31, 1989

[54] PREPARATION OF SOLID PHARMACEUTICAL FORMS

[75] Inventors: Hans-Helmut Goertz, Freinsheim; Roger G. Klimesch, Alsbach-Haehnlein; Klaus Laemmerhirt, Boehl-Iggelheim; Siegfried Lang, Ludwigshafen; Axel Sanner, Frankenthal; Reinhard Spengler, Ludwigshafen, all of Fed. Rep. of Germany

[73] Assignee: BASF Aktiengesellschaft, Fed. Rep. of Germany

[21] Appl. No.: 34,938

[22] Filed: Apr. 6, 1987

[30] Foreign Application Priority Data

Apr. 11, 1986 [DE] Fed. Rep. of Germany ....... 3612212

[51] Int. Cl.$^4$ ................................................. A61K 9/20
[52] U.S. Cl. .................................... 424/465; 424/467; 424/468; 424/80
[58] Field of Search ................. 424/464, 80, 465, 486, 424/487, 467, 468

[56] References Cited

U.S. PATENT DOCUMENTS

| 3,089,818 | 5/1963 | Stone | 167/65 |
| 3,432,592 | 3/1969 | Speiser | 424/19 |
| 4,631,284 | 12/1986 | Salpekar et al. | 514/849 X |
| 4,661,521 | 4/1987 | Salpekar et al. | 424/465 X |

FOREIGN PATENT DOCUMENTS 1137009 9/1962 Fed. Rep. of Germany .
1388786 3/1975 United Kingdom .

OTHER PUBLICATIONS

P. Speiser, Pharmaceutica Acta Helv., 41 (1966), 340.
R. Voight, Lehrbuch der Pharmazeutischen Technologie, 5th Edition, Verlag Chemie, Weinheim, 1984, pp. 221-222.
Tachibana & A. Nakamura, Kolloid Zeitschrift and Zeitschrift fur Polymere, 203 (1965), 130.
M. Mayersohn et al., J. Pharm. Sci. 55 (1966), 1323.
W. Scholten, Arzn. Forschung 14 (1964), 469.
El-Egakey, Soliva, and Speiser, Pharmaceutica Acta Helvetiae, vol. 46, (1971), 31-54.

*Primary Examiner*—Michael Lusignan
*Attorney, Agent, or Firm*—Keil & Weinkauf

[57] ABSTRACT

Process for the preparation of solid pharmaceutical forms by mixing one or more pharmaceutical active compounds with one or more fusible, pharmacologically tolerated binders and, if required, other conventional pharmaceutical auxiliaries, at from 50° to 180° C., and subjecting the mixture to injection molding or extrusion and shaping, wherein the fusible binder used is a NVP polymer which contains not less than 20% by weight of NVP as copolymerized units, and, where they are present, all of whose comonomers contain nitrogen and/or oxygen.

9 Claims, No Drawings

PREPARATION OF SOLID PHARMACEUTICAL FORMS

The present invention relates to a process for the preparation of solid pharmaceutical forms which in an n-vinylpyrrolid-2-one(NVP) polymer as a binder, by injection molding or extrusion and shaping.

Conventional tabletting machines operate by a cyclic process using punches and dies. The process requires thoroughly premixed and specially prepared tabletting materials and the overall process is therefore a multistage one and is expensive. The production of solid pharmaceutical forms with controlled release of active compound is particularly expensive. This may require retardation measures on the one hand and measures for improving the absorption of active compounds on the other hand.

One possible method for improving the absorption of sparingly soluble active compounds is to use solid solutions of the active compounds in water-soluble polymers. The known solid solutions of this type in NVP polymers were prepared by dissolving the active compound and the polymer together in an organic solvent and removing the latter. As a rule, in order to dissolve both the hydrophobic compound and the hydrophilic polymer, chlorohydrocarbons were required. Complete removal of these solvents is very expensive. In order to avoid environmental pollution, the solvents must again be removed as completely as possible from the waste air, which in turn is very expensive. Processes of this type are described in, for example, U.S. Pat. No. 3,089,818; T. Tachibana and A. Nakamura, Kolloid Zeitschrift and Zeitschrift für Polymere, 203 (1965), 130; Japanese Patent No. 24,379; M. Mayersohn et al., J. Pharm. Sci. 55 (1966), 1323; DE-B-11 37 009; and W. Scholten, Arzn. Forschung 14 (1964), 469.

The extrusion of active compound/polymer mixtures has already been described (cf. for example DE-A No.12 29 248; P. Speiser, Pharmaceutica Acta Helv., 41 (1966), 340 and ibid. 46 (1971), 31). However, in no case were solvent-free NVP polymers melted, let alone extruded, without being mixed with other polymers or with water, and in no case is the formation of a solid solution of a sparingly water-soluble active compound in a water-soluble polymer described.

In R. Voigt, Lehrbuch der pharmazeutischen Technologie, 5th Edition, Verlag Chemie, Weinheim, 1984, pages 221-222, the preparation of solid pharmaceutical formulations by injection molding or extrusion shaping of active compound/thermoplastic mixtures is described in general form but without any specific information, in particular about the type of polymers which are suitable for this purpose. The polymers in question here were without a doubt not highly hydrophilic polymers, such as NVP polymers, since, in the pharmaceutical sector to date, these have been processed not via the dry melt but always as a base with solvents (as a rule water) (cf. for example, British Patent No. 1,388,786).

It is an object of the present invention to provide a simple process for the preparation of solid pharmaceutical forms, preferably with controlled release of active compound.

We have found that this object is achieved by a process for the preparation of solid pharmaceutical forms by mixing one or more pharmaceutical active compounds with one or more fusible, pharmacologically tolerated binders and, if required, other conventional pharmaceutical auxiliaries, at from 50° to 180° C., preferably from 60° to 160° C., and subjecting the mixture to injection molding or extrusion and shaping, wherein the fusible binder used is a solvent-free NVP polymer which has a water content of not more than 3.5% by weight and contains not less than 20, preferably not less than 60, in particular 100, % by weight of NVP as copolymerized units, and, where they are present, all of whose comonomers contain nitrogen and/or oxygen, and, at least when the glass transition temperature of the mixture is above 120° C., an NVP polymer is used which is obtained by polymerization in an organic solvent or using an organic peroxide as an initiator in aqueous solution, and the mixture does not contain any thermoplastics which are sparingly soluble in gastric juice (less than 10% dissolving in 6 hours).

The NVP polymers should contain not less than 20, preferably not less than 60, in particular 100, % by weight of NVP as copolymerized units and have a Fikentscher K value (Cellulose-Chemie 13 (1932), 58–64 and 71–74) of from 10 to 70, preferably from 10 to 50, particularly preferably from 12 to 40, in particular from 12 to 35 and, in the case of NVP homopolymers, preferably from 12 to 35, in particular from 12 to 17.

The polymeric binder must soften or melt in the total mixture of all components at from 50 to 180° C., preferably from 60° to 130° C., so that the melt can be extruded. The glass transition temperature of the mixture must therefore in any case be less than 180° C., preferably less than 130° C. If necessary, it is reduced by conventional pharmacologically acceptable plasticizers, such as long-chain alcohols, ethylene glycol, propylene glycol, trimethylolpropane, triethylene gylcol, butanediols, pentanols, hexanols, polyethylene glycols, aromatic carboxylates (eg. dialkyl phthalates, trimellitates, benzoates or terephthalates), aliphatic dicarboxylates (eg. dialkyl adipates, sebacates, azeleates, citrates or tartrates) or fatty acid esters. The plasticizer preferably accounts for no more than 20% by weight, based on the polymer. Particularly preferred NVP polymers are those which do not require additives of this type, ie. those which, as a mixture with the active ingredient and, if required, conventional pharmaceutical auxiliaries, melt or soften in the desired temperature range even without additives having a specific plasticizing effect. Melting or softening below a certain temperature may be necessary because of possible thermal and/or oxidative damage not only to the active ingredient but also to the NVP polymer. The latter may undergo yellowing on extrusion, and it is for this reason that NVP polymers have not usually been extruded to date. However, there is little danger at extrusion temperatures below 180° C., especially below 130° C., if the polymer has not been prepared in aqueous solution using hydrogen peroxide as an initiator, but has been obtained in an organic solvent or in water using an organic peroxide as an initiator, for example by the process according to German Patent application No. P 36 42 633.4 or by the process described in U.S. Pat. Nos. 4,520,179 and 4,520,180.

If the K value is greater than 17, in particular greater than 30 or even 40 (up to a maximum of 70), and no highly plasticizing component is present, the only suitable copolymers are those having a glass transition temperature Tg of less than 120° C., preferably less than 100° C., or the NVP polymer (including homopolymers) must not have been prepared in water containing $H_2O_2$ as an initiator. This would give rise to polymer terminal groups which result in yellowing at elevated temperatures.

Suitable comonomers are unsaturated carboxylic acids, eg. methacrylic acid, crotonic acid, maleic acid and itaconic acid, and their esters with alcohols of 1 to 12, preferably 1 to 8, carbon atoms, as well as hydroxyethyl or hydroxypropyl acrylate and methacrylate, (meth) acrylamide, the anhydrides and half esters of maleic acid and itaconic acid (the half esters preferably not being formed until after the polymerization), N-vinylcaprolactam and vinyl propionate.

Preferred comonomers are acrylic acid and in particular vinyl acetate. Preferred NVP polymers are therefore those which either contain only NVP or vinyl acetate as the only comonomer or contain not less than 10, preferably not less than 30% by weight thereof as copolymerized units. Some or all of the vinyl acetate and vinyl propionate may be hydrolysed after the polymerization.

Solvent-free means that no organic solvent, in particular no chlorohydrocarbon, is added. Furthermore, thermoplastics which are poorly soluble in gastric juice should not be admixed, and the water content of the NVP polymer should not exceed 3.5% by weight. (This water content is due to spontaneous absorption of moisture from the air and not the inten-tional addition of water.) Higher water contents are harmful in that evaporation of the water after the polymer/active compound extrudate emerges from the die results in porous moldings or may even produce moldings possessing cracks in the surface.

The novel process is suitable, for example, for processing the following active compounds: betamethasone, thiotic acid, sotalol, salbutamol, norfenefrine, silymarin, dihydroergotamine, buflomedil, etofibrate, indometacin, oxazepam, β-acetyl-digoxin, piroxicam, haloperidol, ISMN, amitriptylin, diclofenac, nifedipine, verapamil, pyritinol, nitrendipin, doxycycline, bromhexine, methylprednisolone, clonidine, fenofibrate, allopurinol, pirenzepine, levothyroxin, tamoxifen, metildigoxin, o-(β-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafibrate, ISDN, gallopamil, xantinol nicotinate, digitoxin, flunitrazepam, bencyclane, dexapanthenol, pindolol, lorazepam, diltiazem, piracetam, phenoxymethylpencillin, furosemide, bromazepam, flunarizin, erythromycin, metoclopramide, acemetacin, ranitidin, biperiden, metamizole, doxepin, dipotassium chloroazepate, tetrazepam, estramustine phosphat, terbutaline, captopril, maprotiline, prazosin, atenolol, glibenclamide, cefaclor, etilefrine, cimetidine, theophylline, hydromorphone, ibuprofen, primidone, clobazam, oxaceprol, medroxyprogesterone, flecainid, mgpyridoxal 5-phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, myrtol, bromelaine, prenylamine, salazosulfapyridine, astemizol, sulpiride, benzerazide, dibenzepine, acetylsalicylic acid, miconazol, nystatin, ketoconazole, Na picosulfate, colestyramine, gemfibrocil, rifampicin, fluocortolone, mexiletin, amoxicillin, terfenadrin, mucopolysaccharide polysulfate, triazolam, mianserin, tiaprofenic acid, amezinium metilsulfate, mefloquine, probucol, quinidine, carbamazepine, mg L-aspartate, penbutolol, piretanide, amitriptyline, cyproterone, Na valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate and aescin.

Solid solutions of the following active compounds are particularly preferred: acetaminophen (paracetamol), acetohexamide, acetyldigoxin, acetylsalicylic acid, acromycin, anipamil, benzocaine, β-carotene, chloramphenicol, chlordiazepoxide, chlormadinone acetate, chlorothiazide, cinnarizine, clonazepam, codeine, dexamethasone, diazepam, dicoumarol, digitoxin, digoxin, dihydroergotamine, drotaverine, flunitrazepam, furosemide, gramicidin, griseofulvin, hexobarbital, hydrochlorothiazide, hydrocortisone, hydrofluormethiazide, indomethacin, ketoprofen, lonetil, medazepam, mefruside, methandrostenolon e, methylprednisolone, methylsulfadiazine (sulfaperin), nalidixic acid, nifedipine, nitrazepam, nitrofurantoin, nystatin, estradiol, papaverine, phenacetin, pheno-barbital, phenylbutazone, phenytoin, prednisone, reserpine, spironolactone, streptomycin, sulfadimidine (sulfamethazine), sulfamethizole, sulfamethoxazole, sulfamethoxydiazine (sulfameter), sulfaperin, sulfathiazole, sulfisoxazole, testosterone, tolazamide, tolbutamide, trimethoprim and tyrothricin.

The term solid solutions is familiar to the skilled worker, for example from the literature cited at the outset. In solid solutions of pharmaceutical active compounds in polymers, the active compound is present in the polymer in molecular disperse form.

The formation of solid solutions of the stated active compounds in NVP polymers was not to be foreseen and is all the more surprising since many active compounds which are sparingly soluble in water do not form (molecular disperse) solid solutions in other polymers but are incorporated in the particular polymer in the form of solid particles which can be detected under the electron microscope. In the case of crystalline active compounds, they also exhibit a Debye-Scherrer pattern, in contrast to the solid solutions.

If, in addition to the binders employed according to the invention, further water-soluble, fusible binders are used, the amount of the first-mentioned binders should be not less than 50, preferably not less than 70% by weight, based on all fusible binders used.

For the purposes of the present invention, solid pharmaceutical forms are, for example, tablets, tablet cores, granules and suppositories.

For the purposes of the present invention, pharmaceutical active compounds are all substances which have a pharmaceutical effect and have a very low level of side effects, provided that they do not decompose under the processing conditions. The amount of active compound per dosage unit and the concentration can vary within wide limits, depending on the activity and the rate of release. The only condition is that they are sufficient for achieving the desired effect. For example, the concentration of active compound may be from 0.1 to 95, preferably from 20 to 80, in particular from 30 to 70, % by weight. Combinations of active compounds may also be used. For the purposes of the present invention, vitamins too are active compounds. Active compounds which are sparingly soluble in water are those whose absorption in the gastro intestinal tract is usually unsatisfactory owing to their low solubility.

The active compound or compounds can be mixed with the binders and, where relevant, other conventional pharmaceutical additives before or after melting of the polymeric binder, by a method conventionally used in industry. Mixing is preferably carried out in an extruder having a mixing zone, preferably a twin-screw extruder, or in the screw zone of an injection molding machine.

Shaping may be effected by injection molding or by extrusion followed by shaping of the plastic extrudate, for example by hotface cutting to give granules or molding to give tablets, for example by passing the extrudate between two rollers which are driven in opposite directions and have depressions opposite one another in the roller shell, the form of these depressions determining the tablet shape. Cold-face cutting is also suitable and may be followed by pressing of the granules to give tablets. For the purpose of the present invention, the extrustion includes injection molding.

By varying the type and amount of comonomer, the NVP polymer can, depending on the intended use, be made sufficiently strongly or weakly hydrophilic for the tablets prepared from it to dissolve (rapidly or with a delay) in the mouth (buccal tablets) or in the stomach or not until they reach the intestine, or to swell so that they release the active compound. They are sufficiently swellable when they absorb more than 10% by weight of water on storage at 90% relative humidity. If it is desirable for carboxyl-containing binders to release the active compound only when they reach the alkaline medium of the intestine, the above water absorption applies only to the neutralized form (salt form) of the polymer (in which some or all of the protons of the carboxyl groups have been replaced by ammonium, sodium or potassium ions).

Examples of conventional pharmaceutical auxiliaries, whose total amount may be up to 100% by weight, based on the polymer are extenders, such as silicates or silica, stearic acid or its salts with, for example, magnesium or calcium, methylcellulose, sodium carboxymethylcellulose, talc, sucrose, lactose, cereal or corn starch, potato flour or polyvinyl alcohol, as well as wetting agents, preservatives, disintegrating agents, adsorbents, colorants and flavorings (cf. for example H. Sucker et al., Pharmazeutische Technologie, Thieme-Verlag, Stuttgart 1978).

If desired, the solid pharmaceutical form may also be provided with a conventional coating to improve the appearance and/or the flavor (coated tablets) or additionally to delay the release of active compound. For oral tablets with sustained release of active compound, it may be advantageous to prepare the tablet by one of the known techniques in a closed-cell porous form so that it floats in the stomach and consequently remains there longer.

In the case of solid pharmaceutical forms with rapid release of active compound, the novel process permits substantially freer design of the pharmaceutical form than does the conventional tablet pressing technique. For example, the tablets can be engraved for designation, or virtually any shapes, which are clearly identifiable even by those with impaired vision, may be produced. Certain shapes, for example hemispheres may also be suitable for achieving certain characteristics of active compound release. By extrusion or hot or cold face cutting of the extrudate, it is possible to produce very small-particled and uniformly shaped granules in a simple manner, for example for multiple-unit forms.

In the Examples which follow, parts and percentages are by weight. The active compound release time was determined by the half-change test method.

EXAMPLE 1

45 parts of a copolymer of 60% by weight of N-vinylpyrrolidone and 40% by weight of vinyl acetate, having a K value of 30, 5 parts of stearyl alcohol and 50 parts of theophylline were processed to tablet cores in an injection molding machine at 100° C. The tablet cores obtained were stable to mechanical effects and did not show any abrasion during transportation and packaging. In the half-change test (cf. for example R. Voigt, Lehrbuch der pharmazeut. Technologie, 5th Edit-ion, Verl. Chemie. Weinheim; Deerfield Beach, Florida; Basel, 1984, page 627) in conjunction with the paddle method according to USP 21, the active compound was completely released in the course of from 6 to 8 hours.

EXAMPLE 2

50 parts of the copolymer of example 1 and 50 parts of theophylline were processed to oblong tablets having a length of 1 cm in an injection molding machine at 120° C. In this case too, the tablets thus obtained were stable to mechanical effects and released the active compound completely in the course of from 1 to 2 hours.

EXAMPLE 3

47.5 parts of a copolymer of 60% by weight of N-vinylpyrrolidone and 40% by weight of vinyl acetate, having a K value of 30, 2.5 parts of crosslinked polyvinylpyrrolidone (PVP) as a tablet disintegrator and 50 parts of theophylline were mixed and extruded in a twinscrew extruder. The temperature of each of the five shots was 120° C. The die was at 130° C. The still plastic extrudate was pressed to give oblong tablets with the aid of the apparatus described in the parallel German Application No. P 36 12 211.4. The tablets were stable to mechanical effects and the active compound was released in the course of from 30 to 45 minutes.

EXAMPLE 4

50 parts of a copolymer of 30% by weight of N-Weinheim; vinylpyrrolidone and 70% by weight of vinyl acetate, having a K value of 52, and 50 parts of theophylline were mixed and extruded in a twin-screw extruder. The temperatures of the five shots were 30, 60, 100, 100 and 120° C. The die was likewise heated to 120° C. The still plastic extrudate was pressed to give mechanically stable oblong tablets as described in Example 3. The active compound was completely released in the course of 8 hours.

EXAMPLE 5

47.5 parts of a copolymer of 60% by weight of N-vinylpyrrolidone and 40% by weight of vinyl acetate, having a K value of 30, 2.5 parts of stearyl alcohol and 50 parts of theophylline were melted in an injection molding machine at 100° C. and processed to tablet cores. The mold was left at room temperature. The tablet cores thus produced were stable to mechanical effects, and the active compound was completely released in the course of 6 hours.

In each of the Examples 6 to 11, a mixture of 50% by weight of an NVP homopolymer (PVP) having a Fikentscher K value of from 12 to 60 and 50% by weight of theophylline was processed in a single-screw extruder at the following temperatures:

| Example | K value | T [°C.] | | | | | |
|---|---|---|---|---|---|---|---|
| | | 1st | 2nd | 3rd shot | 4th | 5th | Die |
| 6 | 12 | 115 | 125 | 135 | 135 | 135 | 145 |
| 7 | 17 | 125 | 125 | 135 | 145 | 145 | 155 |
| 8 | 25 | 145 | 155 | 165 | 175 | 175 | 175 |
| 9 | 30 | 150 | 160 | 160 | 170 | 180 | 180 |
| 10 | 60 | 150 | 160 | 160 | 170 | 180 | 180 |
| 11 | 60 | 80 | 100 | 130 | 140 | 150 | 160 |

The active compound in the tablets thus obttained dissolved completely (in simulated gastric juice) in less than 30 minutes in the case of Examples 6 and 7, in the course of from 1 to 2 hours in the case of Examples 8 and 9, and after more than 2 hours in the case of Example 10. In Example 11, the PVP contained 10% by weight of stearyl alcohol. In this case, the time of release was 8 hours.

EXAMPLES 12 TO 14

36 parts of a copolymer of 60% by weight of N-vinylpyrrolidone and 40% by weight of vinyl acetate, having a K value of 30, 4 parts of stearyl alcohol, 40 parts of theophylline and 20 parts of
    starch in Example 12,
    lactose in Example 13 and
    sucrose in Example 14
were mixed in a 6-shot twin-screw extruder and shaped into tablets similarly to Example 1. The temperatures of the shots were 90°, 100°, 110°, 120°, 130° and 130° C., and the temperature of the die was 135° C. The active compound dissolved completely out of the tablets in the course of 6 hours.

EXAMPLE 15

50 parts of the copolymer of Examples 12 to 14 and 50 parts of lithium carbonate were processed to tablets on the same apparatus and at the same temperatures as in Examples 12 to 14. These tablets released the active compound (in simulated gastric juice) completely in the course of from 15 to 20 minutes.

EXAMPLE 16

50 parts of the copolymer of Examples 12 to 14 and 50 parts of verapamil were shaped into tablets as described in Examples 12 to 14. The active compound was released in this case in about 3 hours.

The copolymers used for the preparation of solid solutions had the following compositions and K values:
    (A) 60% by weight of NVP and 40% by weight of vinyl acetate; K value about 33.
    (B) 100% by weight of NVP; K value 30.
    (C) 100% by weight of NVP; K value 12.
    (D) 100% by weight of NVP; K value 12.

The polymers B, C and D were prepared according to German Patent Application P 36 42 633.4 in water using an organic peroxide as the initiator.

EXAMPLE 17

3 parts of copolymer A and 1.5 parts of benzocaine were premixed in a plowshare mixer and were extruded in a simple, 6-shot extruder, the individual shots having the following temperatures, proceding toward the die: 30°, 30°, 40°, 50°, 60° and 70° C. The die temperature was likewise 70° C. The extrudate consisted of a solid solution, as was shown by the DebyeScherrer photograph, which did not give the slightest indication of crystallinity. A similar procedure was used for the remaining Examples (cf. Table), and the same result was obtained.

| Example no. | Active compound | Polymer | Active comp./polymer Weight ratio | T1 | T2 | T3 | T4 | T5 | T6 | Die temp. °C. |
|---|---|---|---|---|---|---|---|---|---|---|
| 17a | Benzocaine | A | 1:3 | 20 | 30 | 40 | 40 | 50 | 50 | 50 |
| 18 | Paracetamol | C | 1:3 | 60 | 80 | 100 | 120 | 120 | 120 | 120 |
| 19 | Phenytoin | C | 1:3 | 60 | 80 | 100 | 120 | 120 | 120 | 120 |
| 20 | Benzocaine | C | 1:3 | 50 | 50 | 60 | 60 | 70 | 80 | 90 |
| 21 | Indomethacin | A | 1:3 | 50 | 60 | 70 | 80 | 80 | 80 | 80 |
| 22 | Indomethacin | A | 1:3 | 60 | 80 | 100 | 120 | 120 | 120 | 120 |
| 23 | Anipamil | A | 1:3 | 30 | 30 | 40 | 50 | 50 | 60 | 60 |
| 24 | Anipamil | C | 1:3 | 30 | 30 | 40 | 50 | 50 | 60 | 60 |
| 25 | Benzocaine | A | 1:1 | 30 | 30 | 40 | 500 | 50 | 60 | 60 |
| 26 | Benzocaine | B | 1:1 | 30 | 30 | 40 | 500 | 50 | 60 | 60 |
| 27 | Benzocaine | C | 1:1 | 30 | 30 | 40 | 50 | 50 | 60 | 60 |
| 28 | Phenytoin | A | 1:3 | 60 | 80 | 100 | 120 | 120 | 120 | 130 |
| 29 | Paracetamol | A | 1:3 | 60 | 80 | 100 | 120 | 120 | 120 | 130 |
| 30 | Sulfathiazole | A | 1:1 | 70 | 90 | 100 | 100 | 100 | 100 | 130 |
| 31 | Benzocaine | A | 1:3 | 50 | 50 | 60 | 60 | 70 | 80 | 90 |
| 32 | Benzocaine | C | 1:3 | 50 | 50 | 60 | 60 | 70 | 80 | 80 |
| 33 | Sulfathiazole | C | 1:3 | 70 | 90 | 100 | 100 | 100 | 100 | 120 |
| 34 | Benzocaine | A | 1:9 | 30 | 40 | 50 | 60 | 60 | 70 | 70 |
| 35 | Benzocaine | A | 1:6 | 50 | 60 | 70 | 80 | 85 | 85 | 85 |
| 36 | Benzocaine | C | 1:9 | 30 | 30 | 40 | 50 | 60 | 60 | 60 |
| 37 | Benzocaine | C | 1:6 | 30 | 40 | 60 | 60 | 70 | 70 | 70 |
| 38 | Benzocaine | B | 1:9 | 60 | 70 | 90 | 90 | 90 | 100 | 100 |
| 39 | Benzocaine | B | 1:6 | 60 | 80 | 80 | 100 | 120 | 120 | 120 |
| 40 | Benzocaine | B | 1:3 | 60 | 80 | 80 | 100 | 120 | 120 | 120 |
| 41 | Benzocaine | B | 1:1 | 60 | 80 | 95 | 100 | 120 | 135 | 140 |
| 42 | Phenytoin | A | 1:9 | 60 | 70 | 90 | 90 | 90 | 100 | 100 |
| 43 | Phenytoin | A | 1:6 | 60 | 70 | 90 | 100 | 100 | 100 | 100 |
| 44 | Phenytoin | C | 1:9 | 60 | 70 | 90 | 90 | 100 | 100 | 100 |
| 45 | Phenytoin | C | 1:6 | 60 | 70 | 90 | 100 | 100 | 100 | 100 |
| 46 | Phenytoin | B | 1:9 | 60 | 80 | 110 | 130 | 150 | 150 | 150 |
| 47 | Phenytoin | B | 1:6 | 60 | 80 | 110 | 130 | 150 | 160 | 160 |
| 48 | Phenytoin | B | 1:3 | 60 | 80 | 110 | 120 | 150 | 160 | 170 |

-continued

| Example no. | Active compound | Polymer | Active comp./ polymer Weight ratio | T1 | T2 | T3 | T4 | T5 | T6 | Die temp. °C. |
|---|---|---|---|---|---|---|---|---|---|---|
| 49 | Phenytoin | B | 1:1 | 60 | 80 | 125 | 150 | 160 | 175 | 180 |

T1 to T6 are the temperatures of shots 1 to 6 in °C.

EXAMPLE 50

Examples 18, 19 and 20 were repeated on an injection molding machine at a die temperature of 130° C. Tablets consisting of solid solutions were obtained.

EXAMPLE 51

Vitamin C, as the active compound, was mixed in a weight ratio of 1:1 with the following NVP polymers in a twin-screw extruder, the mixture was extruded at the temperatures stated in the Table for shots 1 to 6 and for the die, and the extrudate was shaped into tablets via a calender, according to the parallel German application No. P 36 12 211.4.

(a) Copolymer of 60% by weight of NVP and 40% by weight of vinyl acetate; K value about 33.

(b) 90% by weight of copolymer (a) and 10% by weight of stearyl alcohol.

(c) Homopolymer of NVP; K value 17.

|     | T1 | T2 | T3  | T4  | T5  | T6  | Die    |
|-----|----|----|-----|-----|-----|-----|--------|
| (a) | 60 | 80 | 100 | 110 | 120 | 120 | 120° C.|
| (b) | 60 | 80 | 80  | 100 | 100 | 110 | 110° C.|
| (c) | 60 | 80 | 100 | 110 | 120 | 120 | 125° C.|

In all three cases, the vitamin was liberated in water in the course of from 1 to 2 hours. During the processing described, it did not undergo any decomposition at all and, in this form, was protected from the effects of light and atmospheric oxygen when stored for a prolonged period.

We claim:

1. A process for the preparation of a solid pharmaceutical form by mixing one or more pharmaceutical active compounds with one or more fusible pharmacologically tolerated binders and subjecting the mixture to injection molding or extrusion and shaping at from 50° to 180° C., wherein the fusible binder used is a solvent-free N-vinylpyrrolidone polymer which has a water content of not more than 3.5% by weight and contains not less than 20% by weight of N-vinylpyrrolid-2-one (as copolymerized units, all copolymerized comonomers contain) nitrogen and/or oxygen and, at least when the glass transition temperature of the mixture is above 120° C., N-vinylpyrrolidone polymer is used which is obtained by polymerization in an organic solvent or using an organic peroxide as an initiator in aqueous solution, and the mixture does not contain any thermoplastics which are sparingly soluble in gastric juice.

2. A process as defined in claim 1, wherein the polymeric binder used contains not less than 60% by weight of N-vinylpyrrolidone as copolymerized units.

3. A process as defined in claim 1, wherein plasticizers are used in an amount of not more than 20% by weight, based on the N-vinylpyrrolidone polymer.

4. A process as defined in claim 1, wherein a polymeric binder used consists of N-vinylpyrrolidone or contains, in addition to N-vinyl-pyrrolidone, only vinyl acetate as copolymerized units.

5. A process as defined in claim 1, wherein a polymeric binder is used whose comonomers are selected from the following group: acrylic acid, meth-acrylic acid, crotonic acid, maleic acid, maleic anhydride, itaconic acid, itaconic anhydride and esters of the stated acids or half esters of the stated dicarboxylic acids with alcohols of 1 to 12 carbon atoms, and hydroxyethyl and hydroxypropyl acrylate and methacrylate, acrylamide, methacrylamide, N-vinylcaprolactam and vinyl propionate.

6. A process as defined in claim 1, wherein the active compound used is sparingly soluble in water, dissolves in the polymer melt without the addition of a solvent or water to give a molecular disperse solution, and forms a solid solution after the melt solidifies.

7. A process as defined in claim 1, wherein one or more active compounds from the following group are used: acetaminophen (paracetamol), acetohexamide, acetyldigoxin, acetylsalicylic acid, acromycin, anipamil, benzocaine, β-carotene, chloramphenicol, chlordiazepoxide, chlormadinone acetate, chlorothiazide, cinnarizine, clonazepam, codeine, dexamethasone, diazepam, dicoumarol, digitoxin, digoxin, dihydroergotamine, drotaverine, flunitrazepam, furosemide, gramicidin, griseofulvin, hexobarbital, hydrochlorothiazide, hydrocortisone, hydrofluormethiazide, indomethacin, ketoprofen, lonetil, medazepam, mefruside, methandrostenolone, methylprednisolone, methylsulfadiazine (sulfaperin), nalidixic acid, nifedipine, nitrazepam, nitrofurantoin, nystatin, estradiol, papaverine, phenacetin, phenobarbital, phenylbutazone phenytoin, prednisone, reserpine, spironolactone, streptomycin, sulfadimidine (sulfamethazine), sulfamethizole, sulfamethoxazole, sulfamethoxydiazine (sulfameter), sulfaperin, sulfathiazole, sulfisoxazole, testosterone, tolazamide, tolbutamide, trimethoprim, tyrothricin.

8. A process as defined in claim 1, wherein a N-vinylpyrrolidone polymer having a Fikentscher K value of from 10 to 50 is used.

9. A process as defined in claim 1, wherein a N-vinylpyrrolidone polymer having a Fikentscher K value of from 12 to 35 is used.

* * * * *